(12) United States Patent
Wang et al.

(10) Patent No.: US 11,568,805 B2
(45) Date of Patent: Jan. 31, 2023

(54) DISPLAY DEVICE AND DATA MONITORING METHOD

(71) Applicants: CHENGDU BOE OPTOELECTRONICS TECHNOLOGY CO., LTD., Sichuan (CN); BOE TECHNOLOGY GROUP CO., LTD., Beijing (CN)

(72) Inventors: Yangpeng Wang, Beijing (CN); Yanyan Zhao, Beijing (CN); Yuanyuan Chai, Beijing (CN); Peng Chen, Beijing (CN); Xucong Wang, Beijing (CN)

(73) Assignees: CHENGDU BOE OPTOELECTRONICS TECHNOLOGY CO., LTD., Sichuan (CN); BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 16/642,731

(22) PCT Filed: Aug. 30, 2019

(86) PCT No.: PCT/CN2019/103589
§ 371 (c)(1),
(2) Date: Feb. 27, 2020

(87) PCT Pub. No.: WO2020/043183
PCT Pub. Date: Mar. 5, 2020

(65) Prior Publication Data
US 2020/0402451 A1    Dec. 24, 2020

(30) Foreign Application Priority Data
Aug. 30, 2018    (CN) .......................... 201811001221.5

(51) Int. Cl.
*G09G 3/3208*    (2016.01)
*A61B 5/024*    (2006.01)
(Continued)

(52) U.S. Cl.
CPC ....... *G09G 3/3208* (2013.01); *A61B 5/02427* (2013.01); *A61B 5/6897* (2013.01);
(Continued)

(58) Field of Classification Search
None
See application file for complete search history.

(56) References Cited

U.S. PATENT DOCUMENTS

2011/0272689 A1* 11/2011 Park ................... G02F 1/13338
438/57
2015/0342479 A1* 12/2015 Liu .................... A61B 5/02416
600/479
(Continued)

FOREIGN PATENT DOCUMENTS

CN    104318205 A    1/2015
CN    104706334 A    6/2015
(Continued)

OTHER PUBLICATIONS

Office Action of CN Application No. 201811001221.5 and English translation, dated Jul. 6, 2020, 17 pages.
(Continued)

*Primary Examiner* — Christopher R Lamb
(74) *Attorney, Agent, or Firm* — Muncy, Geissler, Olds & Lowe, P.C.

(57) ABSTRACT

A display device includes a display panel including a display region and a non-display region surrounding the display region, a plurality of a light-emitting units arranged at the display region; a touch circuit connected to the display panel, and configured to detect touch information when the
(Continued)

display panel is touched; a control circuit connected to the touch circuit and the display panel, and configured to control a corresponding light-emitting unit to emit a predetermined light beam in response to the touch information; a photosensing circuit connected to the display panel and the control circuit, and configured to sense the predetermined light beam and convert it into an electric signal; and a data processor connected to the control circuit and the display panel, and configured to process the electric signal acquired by the photosensing circuit through conversion to acquire monitoring data, and display the monitoring data on the display panel.

8 Claims, 5 Drawing Sheets

(51) Int. Cl.
*A61B 5/00* (2006.01)
*G06F 3/041* (2006.01)
*G06F 3/044* (2006.01)

(52) U.S. Cl.
CPC .......... *G06F 3/0412* (2013.01); *G06F 3/0416* (2013.01); *A61B 5/6898* (2013.01); *G06F 3/044* (2013.01); *G09G 2300/0452* (2013.01); *G09G 2360/145* (2013.01)

(56) References Cited

U.S. PATENT DOCUMENTS

| | | | |
|---|---|---|---|
| 2016/0092717 A1 | 3/2016 | Ling | |
| 2017/0035359 A1 | 2/2017 | Qiu et al. | |
| 2017/0220838 A1* | 8/2017 | He | G06F 3/044 |
| 2017/0220844 A1* | 8/2017 | Jones | G06F 1/1684 |
| 2017/0364187 A1* | 12/2017 | Zhai | G06F 3/0446 |
| 2020/0050829 A1* | 2/2020 | Akcasu | G06F 3/0412 |

FOREIGN PATENT DOCUMENTS

| | | |
|---|---|---|
| CN | 206757648 U | 12/2017 |
| CN | 206946506 U | 1/2018 |
| CN | 107958145 A | 4/2018 |
| CN | 107958185 A | 4/2018 |
| CN | 107958193 A | 4/2018 |
| CN | 107958650 A | 4/2018 |
| CN | 207233359 U | 4/2018 |
| CN | 108021854 A | 5/2018 |
| CN | 108064387 A | 5/2018 |
| CN | 108073911 A | 5/2018 |
| CN | 108288639 A | 7/2018 |
| CN | 109214329 A | 1/2019 |

OTHER PUBLICATIONS

International Search Report of PCT/CN2019/103589 and English translation, dated Nov. 28, 2019, 13 pages.

* cited by examiner

DISPLAY DEVICE AND DATA MONITORING METHOD

CROSS-REFERENCE TO RELATED APPLICATIONS

The present application is the U.S. national phase of PCT Application No. PCT/CN2019/103589 filed on Aug. 30, 2019, which claims a priority of the Chinese patent application No. 201811001221.5 filed on Aug. 30, 2018, which are incorporated herein by reference in their entirety.

TECHNICAL FIELD

The present disclosure relates to the field of display technology, in particular to a display device and a data monitoring method.

BACKGROUND

Currently, the concept "full-screen" becomes hotter and hotter, and many domestic and foreign terminal manufactures, panel manufactures and suppliers compete to study and develop the relevant techniques. Usually, a health monitoring module is adhered, from outside, a back surface of a screen, or a non-display region at a front surface of the screen, so as to provide a fixed position for the health monitoring module. In addition, the health monitoring module needs to be encapsulated separately, so it is adverse to a full-screen design without any seams or openings.

SUMMARY

In one aspect, the present disclosure provides in some embodiments a display device, including: a display panel including a display region and a non-display region surrounding the display region, the display panel including a plurality of a light-emitting units arranged at the display region; a touch circuit electrically connected to the display panel, and configured to detect touch information when the display panel is touched by a user; a control circuit electrically connected to the touch circuit and the display panel, and configured to control a corresponding light-emitting unit to emit a predetermined light beam in response to the touch information; a photosensing circuit electrically connected to the display panel and the control circuit, and configured to sense the predetermined light beam and convert it into an electric signal; and a data processor electrically connected to the control circuit and the display panel, and configured to process the electric signal acquired by the photosensing circuit through conversion to acquire monitoring data, and display the monitoring data on the display panel. The touch circuit is further configured to transmit the touch information to the control circuit.

In a possible embodiment of the present disclosure, the touch information at least includes touch position information.

In a possible embodiment of the present disclosure, the control circuit is configured to, upon the receipt of the touch information from the touch circuit, control a light-emitting unit at a touch position to interrupt a normal display operation and emit the predetermined light beam, and when a touch operation has been completed, control the light-emitting unit at the touch position to perform the normal display operation.

In a possible embodiment of the present disclosure, the display panel further includes a plurality of pixel units, each pixel unit includes a plurality of subpixels capable of emitting light beams in different colors, each subpixel corresponds to one of the light-emitting units, and the predetermined light beam is a light beam emitted by a first light-emitting unit corresponding to a subpixel in a first color.

In a possible embodiment of the present disclosure, the predetermined line beam is a green light beam.

In a possible embodiment of the present disclosure, the touch circuit includes a touch layer arranged at a light-exiting side of the display panel and arranged at a position corresponding to the display region.

In a possible embodiment of the present disclosure, the photosensing circuit is arranged at a side of the display panel away from the touch circuit.

In a possible embodiment of the present disclosure, the photosensing circuit includes a plurality of optical sensors arranged at a side of the display panel away from the touch layer and each arranged at a position corresponding to the display region.

In a possible embodiment of the present disclosure, each optical sensor corresponds to at least one pixel units, and the photosensing circuit further includes a first reception circuit configured to receive a control parameter for controlling the optical sensor at the touch position to be turned on or turned off.

In a possible embodiment of the present disclosure, the display panel includes: a base substrate; a driving circuit layer arranged at a side of the base substrate; the light-emitting units arranged at a side of the driving circuit layer away from the base substrate; and an encapsulation layer arranged at a side of the light-emitting unit away from the base substrate. The optical sensors are integrated into the driving circuit layer, or attached to a side of the base substrate away from the light-emitting units.

In a possible embodiment of the present disclosure, the base substrate is provided with a via-hole or a lens structure at a position corresponding to each optical sensor.

In a possible embodiment of the present disclosure, the touch information further includes touch time. The data processor includes: a second reception circuit configured to receive the electric signal from the photosensing circuit, the electric signal including light intensity wave-shaped curves sensed by the photosensing circuit within different time periods; and a data integration circuit configured to integrate the light intensity wave-shaped curves sensed by the photosensing circuit within different time periods in accordance with the electric signal, so as to acquire the monitoring data.

In another aspect, the present disclosure provides in some embodiments a data monitoring method for the above-mentioned display device, including: detecting, by the touch circuit, touch information when the display panel is touched by a user, and transmitting, by the touch circuit, the touch information to the control circuit; controlling, by the control circuit, a corresponding light-emitting unit to emit a predetermined light beam in response to the touch information; sensing, by the photosensing circuit, the predetermined light beam and converting it into an electric signal; and processing, by the data processor, the electric signal acquired by the photosensing circuit through conversion to acquire monitoring data, and displaying the monitoring data on the display panel.

In a possible embodiment of the present disclosure, the controlling, by the control circuit, the corresponding light-emitting unit to emit the predetermined light beam in response to the touch information includes, upon the receipt of the touch information from the touch circuit, controlling, by the control circuit, the light-emitting unit at a touch position to interrupt a normal display operation and emit the predetermined light beam, and when a touch operation has been completed, controlling the light-emitting unit at the touch position to perform the normal display operation.

In a possible embodiment of the present disclosure, the predetermined line beam is a green light beam.

In a possible embodiment of the present disclosure, a light beam emitted by a first light-emitting unit during the touch operation has a fixed intensity.

In a possible embodiment of the present disclosure, prior to sensing, by the photosensing circuit, the predetermined light beam and converting it into the electric signal, the data monitoring method further includes receiving, by the photosensing circuit, a control parameter for controlling the optical sensor at the touch position to be turned on or turned off.

In a possible embodiment of the present disclosure, the data processor is further configured to: receive the electric signal from the photosensing circuit, the electric signal including light intensity wave-shaped curves sensed by the photosensing circuit within different time periods; and integrate the light intensity wave-shaped curves sensed by the photosensing circuit within different time periods in accordance with the electric signal, so as to acquire the monitoring data.

DETAILED DESCRIPTION

The present disclosure will be described hereinafter in conjunction with the drawings and embodiments. The following embodiments are for illustrative purposes only, but shall not be used to limit the scope of the present disclosure.

In the related art, a health monitoring circuit is arranged at a non-display region of a screen, so it is adverse to the full-screen design. An object of the present disclosure is to provide a display device and a data monitoring method, so as to achieve the full-screen design while monitoring in real time such monitoring data as a health index of a user.

As shown in FIGS. 1 to 6, the present disclosure provides in some embodiments a display device, which includes: a display panel 100 including a display region and a non-display region surrounding the display region, the display panel including a plurality of a light-emitting units arranged at the display region; a touch circuit 200 electrically connected to the display panel 100, and configured to detect touch information when the display panel 100 is touched by a user; a control circuit 300 electrically connected to the touch circuit and the display panel 100, and configured to control a corresponding light-emitting unit to emit a predetermined light beam in response to the touch information; a photosensing circuit 400 electrically connected to the display panel 100 and the control circuit 300, and configured to sense the predetermined light beam and convert it into an electric signal; and a data processor 500 electrically connected to the control circuit 300 and the display panel 100, and configured to process the electric signal acquired by the photosensing circuit 400 through conversion to acquire monitoring data, and display the monitoring data on the display panel 100. The touch circuit 200 is further configured to transmit the touch information to the control circuit 300.

Figure 1:
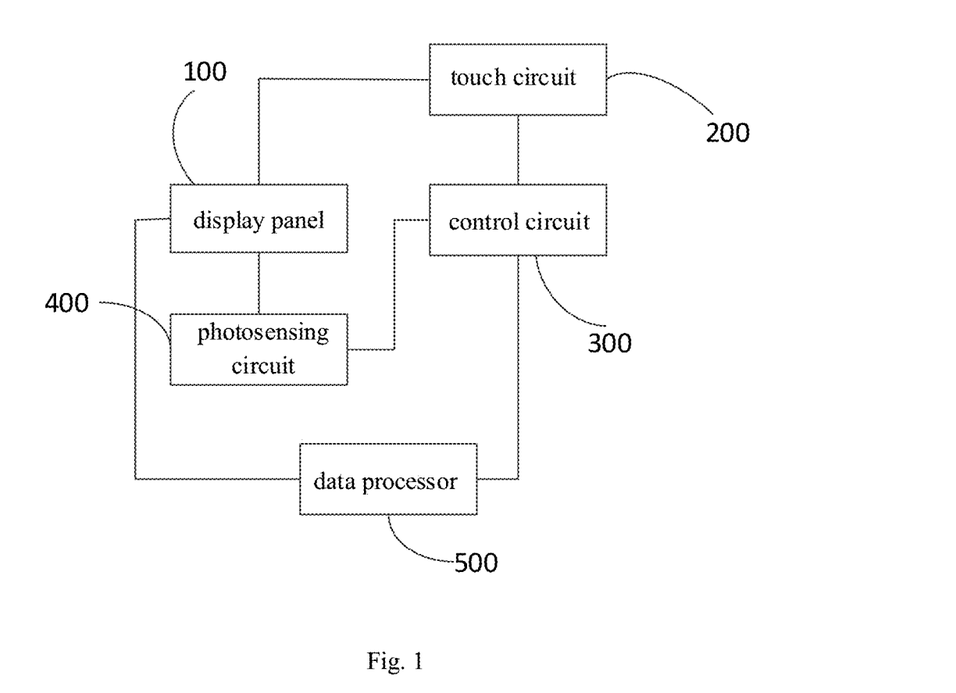
FIG. 1 is a block diagram of a display device according to one embodiment of the present disclosure.

The touch information may include relevant information such as a touch position on the display device, a touch start time and a touch end time. In addition, in the embodiments of the present disclosure, the description will be given hereinafter when the display device is touched by a finger of the user, but the present disclosure shall not be limited thereto, i.e., the scheme in the embodiments of the present disclosure may be applied to a situation where the display device is touched by any part of the user or touched by the user in any form.

In the embodiments of the present disclosure, the photosensing circuit 400 may be provided in a full-screen manner with respect to the entire display region of the display panel 100, and the light-emitting units of the display panel 100 may serve as sensing light sources for the photosensing circuit 400 (i.e., the photosensing circuit 400 may sense light beams emitted by the light-emitting units of the display panel 100). In addition, the touch information, e.g., the touch position of the finger, may be acquired through the touch circuit 200. In this regard, when the display panel is touched by the finger at a certain position, the touch circuit may feed back the touch information to the control circuit 300, and the control circuit 300 may drive a light-emitting unit in a pixel unit at the touch position to emit a light beam. Then, the photosensing circuit 400 may sense the light beam emitted by the light-emitting unit at the touch position, convert it into the electric signal, and transmit the electric signal to the data processor 500. The data processor 500 may process the received electric signal to acquire the monitoring data. When the finger moves away from the display panel, the touch circuit may feed back the touch information indicating that the finger has moved away from the display panel to the control circuit 300. The control circuit 300 may, through a driving chip, enable the light-emitting unit at the touch position not to emit any light beam. At this time, the pixel units at the touch position may display a previous image, i.e., the normal display of the display panel may not be adversely affected.

Hence, according to the display device in the embodiments of the present disclosure, the photosensing circuit 400 may be arranged corresponding to the entire display region, the touch information may be acquired through the touch circuit 200 corresponding to the entire display region, and the light-emitting units of the entire display panel 100 may serve as the sensing light sources for the photosensing circuit 400. As a result, it is able to monitor in real time the monitoring data about the user, e.g., a health index. In addition, the photosensing circuit, the touch circuit and the light-emitting units may be designed in a full-screen manner, and it is unnecessary to separately encapsulate them at the non-display region of the display panel. As compared with the related art where the health monitoring module is separately attached to the non-display region of the display panel, it is able to facilitate the full-screen design.

It should be appreciated that, in the embodiments of the present disclosure, the display panel 100 may be an Organic Light-Emitting Diode (OLED) display panel. Each light-emitting unit may include a cathode, an anode, and a light-emitting layer between the cathode and the anode. Usually, the light-emitting layer may include a hole injection layer, a hole transport layer, an organic light-emitting layer, an electron transport layer, and an electron injection layer. The control circuit 300 may drive the light-emitting layer to emit light through controlling an electric field generated between the cathode and the anode.

In the embodiments of the present disclosure, the control circuit 300 may drive, through the driving chip 310, the light-emitting unit in the pixel unit at the touch position by a finger to emit light, or drive, through the driving chip 310, the pixel unit at the touch position to display normally.

In some embodiments of the present disclosure, the control circuit 300 is configured to, upon the receipt of the touch information from the touch circuit 200, control the light-emitting unit at the touch position to interrupt a normal display operation and emit the predetermined light beam, and when a touch operation has been completed, control the light-emitting unit at the touch position to perform the normal display operation. It should be appreciated that, the display panel 100 may not be limited to the OLED display panel, and it may include a display panel of any other type, e.g., a Quantum Dot Light-Emitting Diode (QLED) display panel or an Active Matrix Organic Light-Emitting Diode (AMOLED) display panel.

Figure 2:
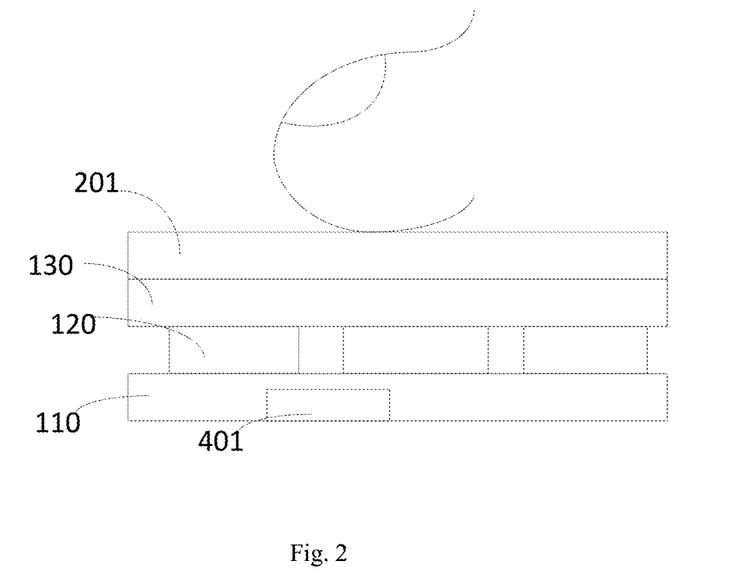
FIG. 2 is a sectional view of a first structure of the display device according to one embodiment of the present disclosure.

It should be further appreciated that, in the embodiments of the present disclosure, the touch circuit 200 may include a touch layer 201 and a touch chip 202. The touch layer 201 may be attached to, or directly formed, at a light-exiting side of the display panel 100, and configured to generate a capacitance change at the touch position. The touch chip 202 is configured to read the capacitance change in the touch layer, convert into the touch information, and feed back the touch information to the control circuit 300.

In a possible embodiment of the present disclosure, each pixel unit includes a plurality of subpixels capable of emitting light beams in different colors. For example, the plurality of subpixels may include a first subpixel, a second subpixel and a third subpixel. Each subpixel may correspond to one of the light-emitting units, and the light-emitting units corresponding to each subpixel may be a first light-emitting unit capable of emitting a light beam in a first color, a second light-emitting unit capable of emitting a light beam in a second color, and a third light-emitting unit capable of emitting a light beam in a third color. For example, each pixel unit may include a red (R) subpixel, a green (G) subpixel and a blue (B) subpixel, or an R subpixel, a G subpixel, a B subpixel and a white (W) subpixel, and each subpixel may correspond to one light-emitting unit.

In a possible embodiment of the present disclosure, the control circuit 300 may control, through the driving chip 301, the light-emitting unit in each pixel unit to emit light or control the pixel unit to display. The control circuit 300 is configured to drive the first light-emitting unit corresponding to the subpixel capable of emitting the light beam in the first color in the pixel unit at the touch position to emit light in accordance with the touch information, and control the light-emitting units corresponding to the subpixels in the pixel unit other than the subpixel capable of emitting the light beam in the first color at the touch position not to emit light.

In a possible embodiment of the present disclosure, the photosensing circuit 400 may sense the light beam in the first color, i.e., sense the light beam in the first color emitted by the first light-emitting unit in the pixel unit, so as to acquire a sensing signal. In actual use, when the display panel is touched by the finger at a certain position, the touch circuit may feed back the touch information to the control circuit 300, and the control circuit 300 may drive the first light-emitting unit in the pixel unit at the touch position to emit the light beam in the first color and drive the light-emitting units in the pixel unit capable of emitting the light beams in the other colors to be turned off. In this way, merely the light beam in the first color may be emitted at the touch position, so it is able to prevent the light beams in the other colors from interfering with the sensing of the light beam in the first color by the photosensing circuit 400, thereby to perform the data monitoring in a more accurate manner.

In a possible embodiment of the present disclosure, the light beam in the first color may be a green light beam, and the light beam emitted by the first light-emitting unit may have a fixed light intensity.

In the embodiments of the present disclosure, the light beam capable of being sensed by the photosensing circuit 400 may be the green light beam, the control circuit 300 may drive the first light-emitting unit at the touch position to emit the green light beam at the fixed light intensity, and the photosensing circuit 400 may merely receive the green light beam at the fixed light intensity. In this regard, the green light at the fixed light intensity may change due to a heart rate of the user, and the photosensing circuit 400 may read the change of the green light beam to acquire the electric signal, thereby to ensure the accuracy of the monitoring data.

It should be appreciated that, in the embodiments of the present disclosure, the light beam in the first color emitted by at least one pixel unit at the touch position may have the fixed light intensity.

It should be further appreciated that, in actual use, when the other data needs to be monitored, the photosensing circuit 400 may be designed in such a manner as to sense the light beam in any other color according to the practical need. Correspondingly, the control circuit 300 may drive the light-emitting unit at the touch position by a finger to emit the light beam in the color capable of being sensed by the photosensing circuit 400, and drive the light-emitting units capable of emitting the light beams in the other colors to be turned off.

In some embodiments of the present disclosure, apart from the light beam in a single color emitted by a single light-emitting unit, a light beam emitted by a plurality of light-emitting units may be used as the predetermined light beam. The photosensing circuit 400 may sense the predetermined light beam, so as to acquire monitoring information, e.g., a relevant parameter capable of reflecting a health state of the user, in accordance with the predetermined light beam reflected by the user's body part at the touch position.

Figure 6:
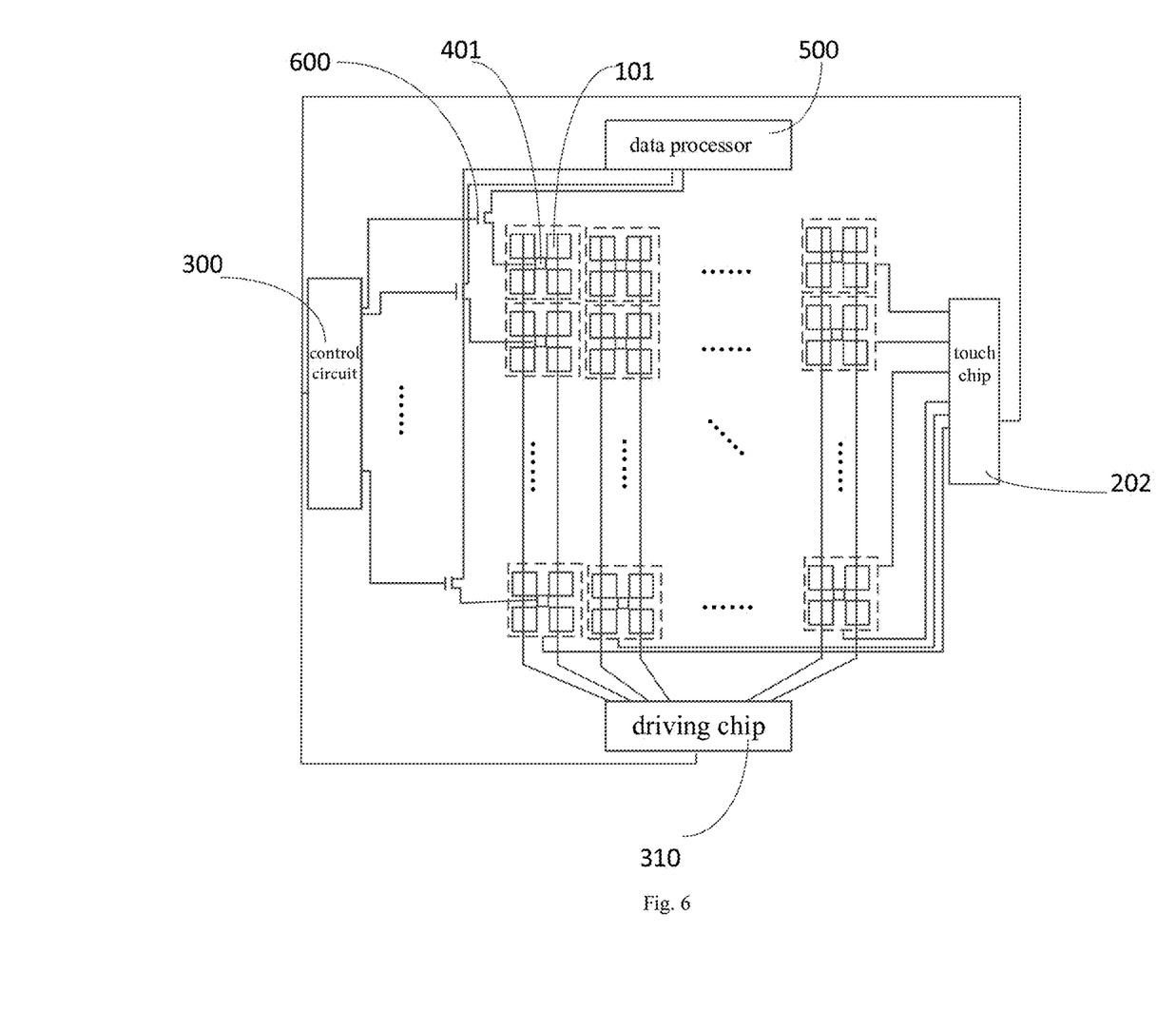
FIG. 6 is a schematic view showing an overall structure of the display device according to one embodiment of the present disclosure.

In a possible embodiment of the present disclosure, as shown in FIG. 6, the photosensing circuit 400 may include a plurality of optical sensors 401 each corresponding to at least one pixel unit 101, and a first reception circuit configured to receive the control parameter and control the optical sensor 401 at the touch position to be turned on or off. The control parameter may include a control parameter generated by the control circuit 300 in accordance with the touch information, or a control parameter inputted by the user.

In the embodiments of the present disclosure, the pixel units 101 of the display panel 100 may be arranged in an array form, the optical sensors 401 may be arranged in an array form too, and each optical sensor 401 may correspond to at least one pixel unit 101. For example, as shown in FIG. 6, one optical sensor 401 may correspond to four pixel units 101 surrounding the optical sensor. Of course, in actual use, the quantity of the pixel units 101 corresponding to one optical sensor 401 will not be particularly defined. In addition, the control circuit 300 may control whether the optical sensor 401 is to be turned on or off (in FIG. 6, a control switch 600 is arranged between the control circuit 300 and each optical sensor 401) in accordance with the touch information from the touch circuit 200. To be specific, in use, when the display panel is touched by the finger at a certain position, the touch circuit 200 may feed back the touch information to the control circuit 300. The control circuit 300 may drive the optical sensor 401 at the touch position to be turned on. When the finger has moved away from the display panel, the touch circuit 200 may feed back the touch information indicating that the finger has moved away from the display panel to the control circuit 300. The control circuit 300 may drive the optical sensor 401 at the touch position to be turned off. In this way, it is able to prevent the photosensing circuit from being in an on state all the time, thereby to reduce the power consumption.

It should be appreciated that, each optical sensor 401 may also not be controlled by the control circuit 300, and instead, it may be in an on state all the time; at this time, the power consumption may increase. Also, each optical sensor 401 may be turned on or off in accordance with the control parameter inputted by the user.

In a possible embodiment of the present disclosure, as shown in FIGS. 2 to 5, the display panel 100 may include: a base substrate (not shown); a driving circuit layer 110 arranged at a side of the base substrate; the light-emitting units 120 arranged on the driving circuit layer 110; and an encapsulation layer 130 for encapsulating the light-emitting units 120. The touch layer 201 of the touch circuit 200 may be arranged on the encapsulation layer 130, and the optical sensors 401 may be integrated into the driving circuit layer 120, or attached to a side of the base substrate away from the light-emitting units 120.

In the embodiments of the present disclosure, the sensing of a reflected light beam is adopted as a data monitoring principle of the display device, i.e., the light beam in the first color emitted by the light-emitting unit may pass through a display surface of the display panel toward the finger, and then the photosensing circuit 400 may sense the light beam in the first color reflected by the finger so as to acquire the monitoring data. Hence, the photosensing circuit 400 may be integrated into the driving circuit layer on the base substrate (as shown in FIGS. 2-4), or attached to a back surface of the entire display panel 100 (as shown in FIG. 5).

Figure 3:
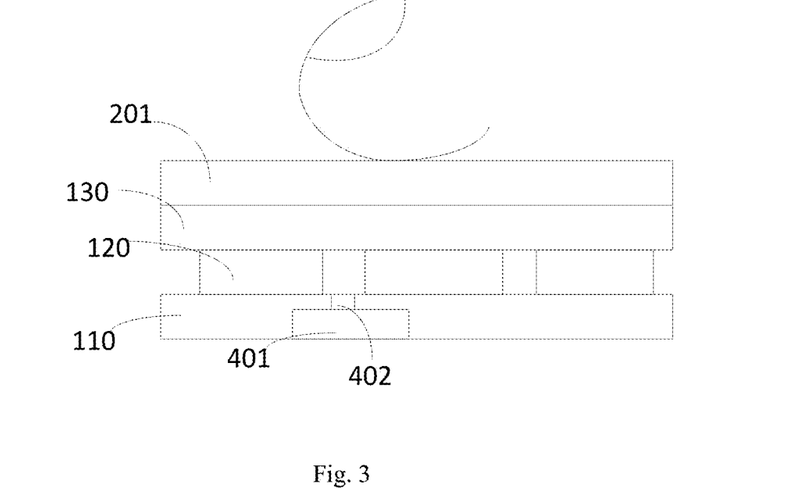
FIG. 3 is another sectional view of a second structure of the display device according to one embodiment of the present disclosure.
Figure 4:
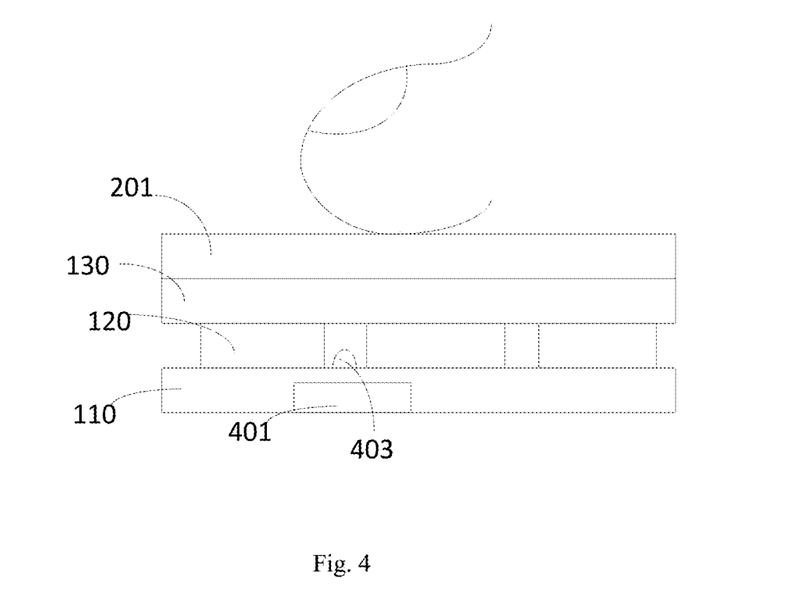
FIG. 4 is yet another sectional view of a third structure of the display device according to one embodiment of the present disclosure.

In a possible embodiment of the present disclosure, as shown in FIGS. 3 and 4, the base substrate may be provided with a via-hole 402 or a lens structure 403 at a position corresponding to each optical sensor 401.

Figure 5:
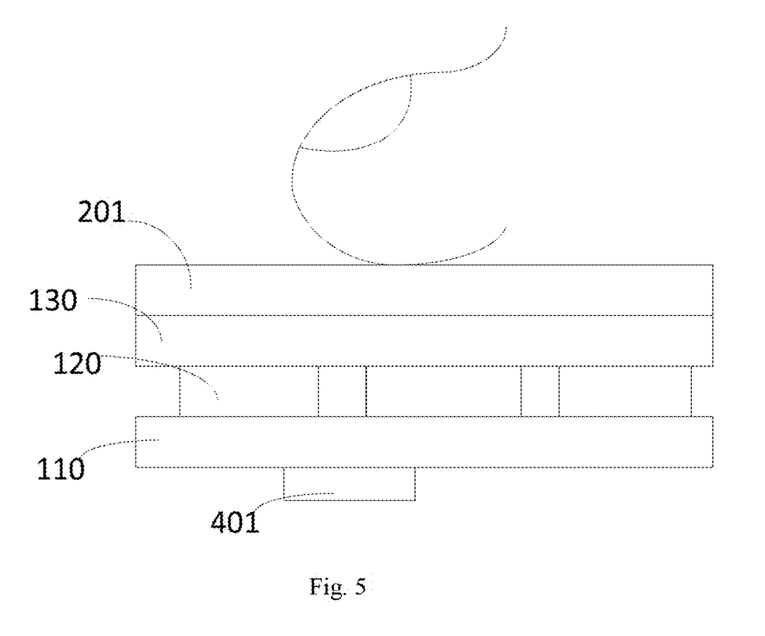
FIG. 5 is still yet another sectional view of a fourth structure of the display device according to one embodiment of the present disclosure.

In the embodiments of the present disclosure, there may exist no special design between the photosensing circuit 400 and the light-emitting layer of the light-emitting unit (as shown in FIGS. 2 and 5), or the via-hole 402 may be formed in the base substrate (as shown in FIG. 3), or the lens structure 403 may be formed at the base substrate (as shown in FIG. 4), so as to remove the interference caused by scattered light.

It should be appreciated that, the structure and size of each optical sensor 401 will not be particularly defined herein, and one or more optical sensors 401 may be provided at a touch region between the finger and the display panel. In a possible embodiment of the present disclosure, an area of the pixel units 101 capable of emitting the green light beam at the fixed light intensity may not be greater than an area of the touch region. In this way, it is able to prevent an image displayed on the display panel from being adversely affected when merely the pixel units 101 emit the light at the touch position.

It should be further appreciated that, in actual use, for the display device such as a mobile phone, the finger of the user may be in contact with the display panel for most of the time, merely with changed touch positions. Hence, the final monitor data may be acquired through fitting a plurality of groups of data. To be specific, the data processor 500 may include: a second reception circuit configured to receive the electric signal from the photosensing circuit 400, the electric signal including light intensity wave-shaped curves sensed by the photosensing circuit 400 within different time periods; and a data integration circuit configured to integrate the light intensity wave-shaped curves sensed by the photosensing circuit 400 within different time periods in accordance with the electric signal, so as to acquire the monitoring data.

Figure 7:
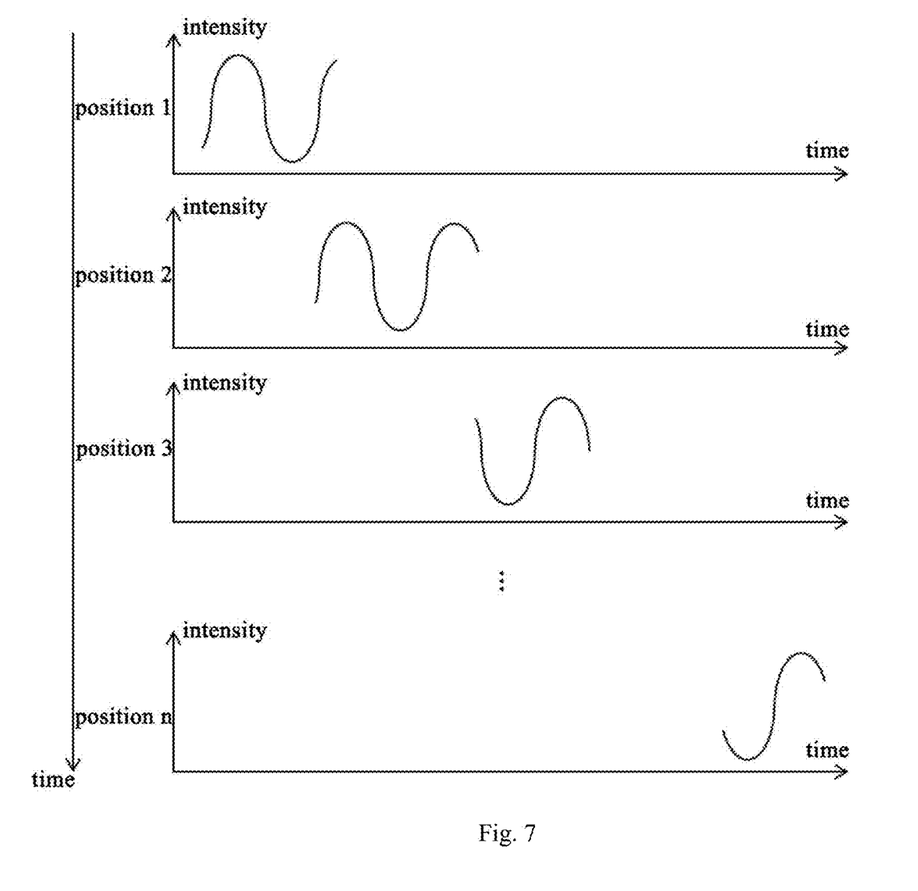
FIG. 7 is a schematic view showing light intensity wave-shaped curves of sensed by a photosensing circuit and received by a data processor within different time periods according to one embodiment of the present disclosure.
Figure 8:
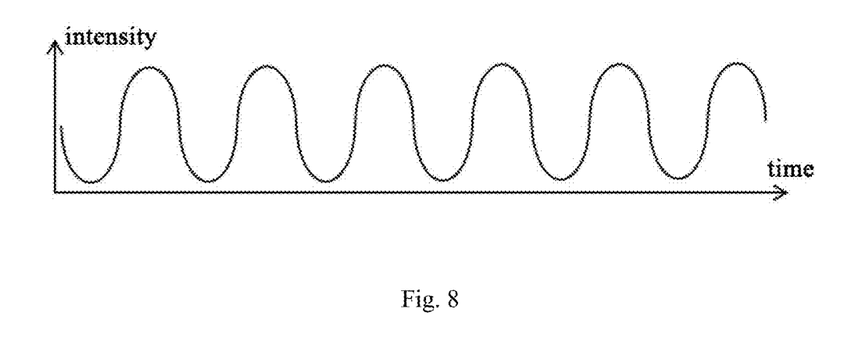
FIG. 8 is a schematic view showing a complete light intensity wave-shaped curve acquired through integrating, by the data processor, the light intensity wave-shaped curves sensed by the photosensing circuit within different time periods according to one embodiment of the present disclosure.

In the embodiments of the present disclosure, as shown in FIGS. 7 and 8, in use, the data processor 500 may acquire the monitoring data within different time periods, integrate the monitoring data acquired within different time periods through fitting, and then calculate the final monitoring data.

Generally speaking, as shown in FIG. 7, the monitoring data acquired within each time period may correspond to one light intensity wave-shaped curve, and the light intensity wave-shaped curves acquired within different time periods may have frequencies and intensities which are not completely the same. Hence, for the light intensity wave-shaped curve within each time period, merely a waveform between a first light intensity extreme point (a valley value) and a last light intensity extreme point (a peak value) may be intercepted, and then the waveforms within all the time periods may be stitched together in a chronological order so as to acquire the complete light intensity wave-shaped curve (as shown in FIG. 8). Based on the complete light intensity wave-shaped curve, it is able to acquire the monitoring data about the health index of the user (e.g., heart rate).

It should be appreciated that, a duration of each time period may be set at a system end when the display device leaves the factory, or selected by the user from some predetermined options.

It should be further appreciated that, in actual use, the data processor 500 may not be limited to the processing mode mentioned hereinabove, and some other processing modes may also be adopted. For example, the data processor 500 may calculate values of sub-indices A1, A2, A3, . . . , An at positions 1, 2, 3, . . . , n when acquiring the light intensity wave-shaped curved within each time period (e.g., the sub-index may be an average value of the light intensities within each time period), and then acquire the monitoring data about the health index of the user (e.g., the heart rate)

in accordance with the statistics calculation of the sub-indices within all the time periods.

The present disclosure further provides in some embodiments a data monitoring method for the above-mentioned display device, which includes: Step S1 of detecting, by the touch circuit 200, touch information when the display panel 100 is touched by a user, and transmitting, by the touch circuit 200, the touch information to the control circuit 300; Step S2 of controlling, by the control circuit 300, a corresponding light-emitting unit to emit a predetermined light beam in response to the touch information; and Step S3 of sensing, by the photosensing circuit 400, the predetermined light beam and converting it into an electric signal.

In a possible embodiment of the present disclosure, the data monitoring method may further include processing, by the data processor 500, the electric signal acquired by the photosensing circuit 400 through conversion to acquire monitoring data, and displaying the monitoring data on the display panel 100.

In the embodiments of the present disclosure, the photosensing circuit 400 may be provided in a full-screen manner with respect to the entire display region of the display panel 100, and the light-emitting units of the display panel 100 may serve as sensing light sources for the photosensing circuit 400 (i.e., the photosensing circuit 400 may sense light beams emitted by the light-emitting units of the display panel 100). In addition, the touch information, e.g., the touch position of the finger and the touch time, may be acquired through the touch circuit 200. In this regard, when the display panel is touched by the finger at a certain position, the touch circuit may feed back the touch information to the control circuit 300, and the control circuit 300 may drive a light-emitting unit in a pixel unit at the touch position to emit a light beam. Then, the photosensing circuit 400 may sense the light beam emitted by the light-emitting unit at the touch position, convert it into the electric signal, and transmit the electric signal to the data processor 500. The data processor 500 may process the received electric signal to acquire the monitoring data. When the finger moves away from the display panel, the touch circuit may feed back the touch information indicating that the finger has moved away from the display panel to the control circuit 300. The control circuit 300 may, through a driving chip, enable the light-emitting unit at the touch position not to emit any light beam. At this time, the pixel units at the touch position may display a previous image, i.e., the normal display of the display panel may not be adversely affected. As a result, it is able to monitor in real time the monitoring data, e.g., the health index of the user, and as compared with the related art, it is able to facilitate the full-screen design for the display device.

In a possible embodiment of the present disclosure, Step S2 may include driving, by the control circuit 300, the first light-emitting unit corresponding to the subpixel capable of emitting the light beam in the first color in the pixel unit 101 at the touch position to emit light, and controlling the light-emitting units corresponding to the subpixels in the pixel unit 101 other than the subpixel capable of emitting the light beam in the first color at the touch position not to emit light.

In a possible embodiment of the present disclosure, the photosensing circuit 400 may sense the light beam in the first color, i.e., sense the light beam in the first color emitted by the first light-emitting unit in the pixel unit 101, so as to acquire a sensing signal. In actual use, when the display panel is touched by the finger at a certain position, the touch circuit may feed back the touch information to the control circuit 300, and the control circuit 300 may drive the first light-emitting unit in the pixel unit 101 at the touch position to emit the light beam in the first color and drive the light-emitting units in the pixel unit 101 capable of emitting the light beams in the other colors to be turned off. In this way, merely the light beam in the first color may be emitted at the touch position, so it is able to prevent the light beams in the other colors from interfering with the sensing of the light beam in the first color by the photosensing circuit 400, thereby to perform the data monitoring in a more accurate manner.

In a possible embodiment of the present disclosure, the light beam in the first color may be a green light beam, and the light beam emitted by the first light-emitting unit may have a fixed light intensity.

In the embodiments of the present disclosure, the light beam capable of being sensed by the photosensing circuit 400 may be the green light beam, the touch circuit 300 may drive the first light-emitting unit at the touch position to emit the green light beam at the fixed light intensity, and the photosensing circuit 400 may merely receive the green light beam at the fixed light intensity. In this regard, the green light at the fixed light intensity may change due to a heart rate of the user, and the photosensing circuit 400 may read the change of the green light beam to acquire the electric signal, thereby to ensure the accuracy of the monitoring data.

It should be appreciated that, in the embodiments of the present disclosure, the light beam in the first color emitted by at least one pixel unit at the touch position may have the fixed light intensity.

It should be further appreciated that, in actual use, when the other data needs to be monitored, the photosensing circuit 400 may be designed in such a manner as to sense the light beam in any other color according to the practical need. Correspondingly, the touch circuit 300 may drive the light-emitting unit at the touch position to emit the light beam in the color capable of being sensed by the photosensing circuit 400, and drive the light-emitting units capable of emitting the light beams in the other colors to be turned off.

In a possible embodiment of the present disclosure, in Step S3, the photosensing circuit 400 may receive the control parameter and control the optical sensor 401 at the touch position to be turned on or off. The control parameter may include a control parameter generated by the control circuit 300 in accordance with the touch information, or a control parameter inputted by the user.

In the embodiments of the present disclosure, the pixel units 101 of the display panel 100 may be arranged in an array form, the optical sensors 401 may be arranged in an array form too, and each optical sensor 401 may correspond to at least one pixel unit 101. For example, as shown in FIG. 6, one optical sensor 401 may correspond to four pixel units 101 surrounding the optical sensor. Of course, in actual use, the quantity of the pixel units 101 corresponding to one optical sensor 401 will not be particularly defined. In addition, the control circuit 300 may control whether the optical sensor 401 is to be turned on or off in accordance with the touch information from the touch circuit 200. To be specific, in use, when the display panel is touched by the finger at a certain position, the touch circuit 200 may feed back the touch information to the control circuit 300. The control circuit 300 may drive the optical sensor 401 at the touch position to be turned on. When the finger has moved away from the display panel, the touch circuit 200 may feed back the touch information indicating that the finger has moved away from the display panel to the control circuit 300. The control circuit 300 may drive the optical sensor 401 at the touch position to be turned off. In this way, it is able to prevent the photosensing circuit from being in an on state all the time, thereby to reduce the power consumption.

It should be appreciated that, each optical sensor 401 may also not be controlled by the control circuit 300, and instead, it may be in an on state all the time; at this time, the power consumption may increase. Also, each optical sensor 401 may be turned on or off in accordance with the control parameter inputted by the user.

In a possible embodiment of the present disclosure, Step S4 may include: receiving, by the data processor 500, the electric signal from the photosensing circuit 400, the electric signal including light intensity wave-shaped curves sensed by the photosensing circuit 400 within different time periods; and integrating the light intensity wave-shaped curves sensed by the photosensing circuit 400 within different time periods in accordance with the electric signal, so as to acquire the monitoring data.

In the embodiments of the present disclosure, as shown in FIGS. 7 and 8, in use, the data processor 500 may acquire the monitoring data within different time periods, integrate the monitoring data acquired within different time periods through fitting, and then calculate the final monitoring data.

Generally speaking, the monitoring data acquired within each time period may correspond to one light intensity wave-shaped curve, and the light intensity wave-shaped curves acquired within different time periods may have frequencies and intensities which are not completely the same. Hence, for the light intensity wave-shaped curve within each time period, merely a waveform between a first light intensity extreme point (a valley value) and a last light intensity extreme point (a peak value) may be intercepted, and then the waveforms within all the time periods may be stitched together in a chronological order so as to acquire the complete light intensity wave-shaped curve. Based on the complete light intensity wave-shaped curve, it is able to acquire the monitoring data about the health index of the user (e.g., heart rate).

It should be appreciated that, a duration of each time period may be set at a system end when the display device leaves the factory, or selected by the user from some predetermined options.

It should be further appreciated that, in actual use, the data processor 500 may not be limited to the processing mode mentioned hereinabove, and some other processing modes may also be adopted. For example, the data processor 500 may calculate values of sub-indices A1, A2, A3, . . . , An at positions 1, 2, 3, . . . , n when acquiring the light intensity wave-shaped curved within each time period (e.g., the sub-index may be an average value of the light intensities within each time period), and then acquire the monitoring data about the health index of the user (e.g., the heart rate) in accordance with the sub-indices within all the time periods.

The above embodiments are for illustrative purposes only, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A display device, comprising:
a display panel comprising a display region and a non-display region surrounding the display region, the display panel comprising a plurality of a light-emitting units arranged at the display region;
a touch circuit electrically connected to the display panel, and configured to detect touch information when the display panel is touched by a user;
a control circuit electrically connected to the touch circuit and the display panel, and configured to control a corresponding light-emitting unit to emit a predetermined light beam in response to the touch information;
a photosensing circuit electrically connected to the display panel and the control circuit, and configured to sense the predetermined light beam and convert it into an electric signal; and
a data processor electrically connected to the control circuit and the display panel, and configured to process the electric signal acquired by the photosensing circuit through conversion to acquire monitoring data, and display the monitoring data on the display panel,
wherein the touch circuit is further configured to transmit the touch information to the control circuit,
wherein the control circuit is configured to, upon the receipt of the touch information from the touch circuit, control a light-emitting unit at a touch position to interrupt a normal display operation and emit the predetermined light beam, and when a touch operation has been completed, control the light-emitting unit at the touch position to perform the normal display operation,
wherein the display panel further comprises a plurality of pixel units, each pixel unit comprises a plurality of subpixels capable of emitting light beams in different colors, each subpixel corresponds to one of the light-emitting units, and the predetermined light beam is a light beam emitted by a first light-emitting unit corresponding to a subpixel in a first color, the predetermined light beam has a fixed light intensity,
wherein the touch circuit comprises a touch layer arranged at a light-exiting side of the display panel and arranged at a position corresponding to the display region,
wherein the photosensing circuit comprises a plurality of optical sensors arranged at a side of the display panel away from the touch layer and each arranged at a position corresponding to the display region,
wherein the display panel comprises:
a base substrate;
a driving circuit layer arranged at a side of the base substrate;
the light-emitting units arranged at a side of the driving circuit layer away from the base substrate; and
an encapsulation layer arranged at a side of the light-emitting unit away from the base substrate, wherein the optical sensors are attached to a side of the base substrate away from the light-emitting units,
wherein the control circuit drives the first light-emitting unit in the pixel unit at the touch position to emit a green light beam at a fixed light intensity and drive the light-emitting units in the pixel unit capable of emitting the light beams in other colors to be turned off,
wherein one optical sensor corresponds to four pixel units surrounding the optical sensor, and
wherein an area of the pixel units capable of emitting the green light beam at the fixed light intensity is not greater than an area of a touch region.

2. The display device according to claim 1, wherein the touch information at least comprises touch position information.

3. The display device according to claim 1, wherein each optical sensor corresponds to at least one pixel units, and the photosensing circuit further comprises a first reception circuit configured to receive a control parameter for controlling the optical sensor at the touch position to be turned on or turned off.

4. The display device according to claim 1, wherein the touch information further comprises touch time, wherein the data processor comprises: a second reception circuit configured to receive the electric signal from the photosensing circuit, the electric signal comprising light intensity wave-shaped curves sensed by the photosensing circuit within different time periods; and a data integration circuit configured to integrate the light intensity wave-shaped curves sensed by the photosensing circuit within different time periods in accordance with the electric signal, so as to acquire the monitoring data.

5. A data monitoring method applied for the display device according to claim 1, comprising:
    detecting, by the touch circuit, touch information when the display panel is touched by a user, and transmitting, by the touch circuit, the touch information to the control circuit;
    controlling, by the control circuit, a corresponding light-emitting unit to emit a predetermined light beam in response to the touch information;
    sensing, by the photosensing circuit, the predetermined light beam and converting it into an electric signal; and
    processing, by the data processor, the electric signal acquired by the photosensing circuit through conversion to acquire monitoring data, and displaying the monitoring data on the display panel.

6. The data monitoring method according to claim 5, wherein the controlling, by the control circuit, the corresponding light-emitting unit to emit the predetermined light beam in response to the touch information comprises:
    upon the receipt of the touch information from the touch circuit, controlling, by the control circuit, the light-emitting unit at a touch position to interrupt a normal display operation and emit the predetermined light beam, and when a touch operation has been completed, controlling the light-emitting unit at the touch position to perform the normal display operation.

7. The data monitoring method according to claim 5, wherein prior to sensing, by the photosensing circuit, the predetermined light beam and converting it into the electric signal, the data monitoring method further comprises receiving, by the photosensing circuit, a control parameter for controlling the optical sensor at the touch position to be turned on or turned off.

8. The data monitoring method according to claim 7, wherein the data processor is further configured to: receive the electric signal from the photosensing circuit, the electric signal comprising light intensity wave-shaped curves sensed by the photosensing circuit within different time periods; and integrate the light intensity wave-shaped curves sensed by the photosensing circuit within different time periods in accordance with the electric signal, so as to acquire the monitoring data.

* * * * *